United States Patent [19]
Dreoni et al.

[11] Patent Number: 5,322,958
[45] Date of Patent: Jun. 21, 1994

[54] CATALYTIC PROCEDURE FOR THE PREPARATION OF ORGANIC CARBONATES

[75] Inventors: Daniele Dreoni, Bologna; Franco Rivetti, Milan; Daniele Delledonne, Oleggio, all of Italy

[73] Assignee: Enichem Synthesis, S.p.A., Palermo, Italy

[21] Appl. No.: 20,666

[22] Filed: Feb. 22, 1993

[30] Foreign Application Priority Data

Feb. 26, 1992 [IT] Italy ............................ 92 A/000417

[51] Int. Cl.$^5$ ............................................. C07C 69/96
[52] U.S. Cl. .................................................. 558/277
[58] Field of Search ......................................... 558/277

[56] References Cited

U.S. PATENT DOCUMENTS

| | | |
|---|---|---|
| 3,846,468 | 11/1974 | Perrotti et al. |
| 3,980,690 | 9/1976 | Cipriani et al. |
| 4,218,391 | 8/1980 | Romano et al. |
| 4,318,862 | 3/1982 | Romano et al. |
| 4,361,519 | 11/1982 | Hallgren |
| 4,625,044 | 11/1986 | Curnutt |
| 4,900,705 | 2/1990 | Sawicki et al. |
| 5,004,827 | 4/1991 | Curnutt |

FOREIGN PATENT DOCUMENTS

| | | |
|---|---|---|
| 0425197 | 5/1991 | European Pat. Off. |
| 0463678 | 1/1992 | European Pat. Off. |
| 3212535 | 10/1983 | Fed. Rep. of Germany |
| WO8707601 | 12/1987 | PCT Int'l Appl. |

2148881  6/1985  United Kingdom .

OTHER PUBLICATIONS

GB 2148881; WPI Acc. No. 85-136922/23 Database WPI, Derwent Publications Ltd, GB, 1985.
DE 3212535; WPI Acc. No. 83-790139/42 Database WPI, Derwent Publications Ltd. GB, 1983.

*Primary Examiner*—M. Lee
*Assistant Examiner*—Michael G. Ambrose
*Attorney, Agent, or Firm*—George P. Hoare, Jr.

[57] ABSTRACT

Catalytic procedure in gas phase for the preparation of a symmetrical or asymmetrical organic carbonate having the general formula (I):

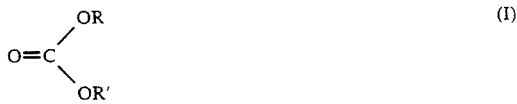

wherein R and R', the same or different, represent a $C_1$-$C_4$ alkyl radical, linear or branched, which includes reacting at least one alcohol having the general formula (II):

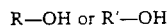

with carbon monoxide and oxygen in the presence of a catalyst composed of oxides, salts or complexes of cobalt.

11 Claims, No Drawings

CATALYTIC PROCEDURE FOR THE PREPARATION OF ORGANIC CARBONATES

The present invention relates to a catalytic procedure for the preparation of organic carbonates.

More specifically, the present invention relates to a catalytic procedure in gas phase for the preparation of organic carbonates.

Organic carbonates are useful intermediates in the chemical field, and among these dimethyl carbonate is widely used as an additive for fuels, as an organic solvent and in the synthesis of other carbonates, both alkyl and aryl. In addition, organic carbonates can be used as synthetic lubricants, monomers for organic glass, plasticizers or as reagents in methylation and carbomethoxylation reactions for the preparation of phenol ethers, quaternary salts of ammonium, ureas, urethanes, isocyanates and polycarbonates.

The typical procedure for the preparation of alkyl carbonates consists in the reaction of an alcohol with phosgene, as described for example in Kirk-Othmer, "Encyclopedia of Chemical Technology", 3rd ed., N.4, page 758. This procedure, however, has numerous technical problems (elimination of the hydrochloric acid produced in the reaction), as well as safety problems owing to the use of phosgene.

To overcome these drawbacks, alternative synthesis procedures have been proposed, such as the oxidative carbonylation of methanol in the presence of catalysts based on palladium (U.S. Pat. No. 4,361,519; DE 3.212.535 and GB 2.148.881), based on copper (U.S. Pat. Nos. 3,846,468; 4,218,391; 4,318,862) or based on cobalt (Italian Patent Application No. 20809 A/90 and No. 000374 A/91).

The procedures of the known art have some disadvantages however owing to the fact that the reaction is carried out in a liquid phase and under basically homogeneous catalysis conditions. In fact, in the above procedures, the reaction system has a high sensitivity to the water produced which reduces both the selectivity of the carbon monoxide towards the formation of dimethyl carbonate, and the reaction rate; there is difficulty in separating the catalyst and reaction products and, when a catalyst based on copper is used, there is high corrosion of the reaction medium.

To overcome these disadvantages, procedures in gas phase have been proposed wherein the organic carbonates are produced starting from methanol, carbon monoxide and oxygen operating in the presence of an oxidative carbonylation catalyst. Examples of these catalysts are: supported salts and complexes of copper, systems which are generally rapidly disactivated and, in some cases, release hydrochloric acid and form corrosive mixtures (U.S. Pat. No. 3,980,690; IT 1.092.951; U.S. Pat. Nos. 4,625,044; 5,004,827; 4,900,705); supported salts of palladium, systems which combined with nitrogen oxides, nitritoalkanes, oxygen, carbon monoxide, produce organic carbonates but cause technical problems due to the use of nitritoalkanes and nitrogen oxides (EP 425.197).

The Applicant has now found that a catalytic procedure in gas phase for the preparation of organic carbonates which does not have the above disadvantages can be carried out using a suitable catalyst based on cobalt.

The present invention consequently relates to a catalytic procedure in gas phase for the preparation of a symmetrical or asymmetrical organic carbonate having the general formula (I):

wherein R and R', the same or different, represent a $C_1-C_4$ alkyl radical, linear or branched, which includes reacting at least one alcohol having the general formula (II):

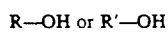

with carbon monoxide and oxygen in the presence of a catalyst composed of the oxides, salts, more preferably non-halogenated, or complexes of cobalt.

More specifically, when a single aliphatic alcohol having general formula (II) is used in the carbonylation reaction, the procedure of the present invention may be schematized as follows:

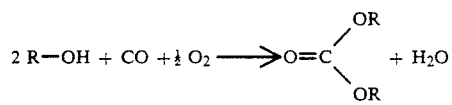

wherein R has the same meaning as described above.

The molar ratio between the carbon monoxide and the alcohol is between 1:1 and 1000:1, in particular between 1:1 and 100:1, even better between 1:1 and 20:1.

The molar ratio between the oxygen and alcohol is between 2:1 and 1:100, in particular between 1:1 and 1:10.

The ratio in volume between the oxygen and carbon monoxide is between 1:1 and 1:100, in particular between 1:1 and 1:20.

The oxygen may be either pure or mixed with an inert gas such as nitrogen and argon. It is preferable, even if not necessary, to maintain a concentration of the oxygen in the whole reaction mixture of less than 10% (in volume), in order to avoid the formation of explosive mixtures.

The reaction is carried out at a temperature ranging from 20° C. to 250° C., in particular from 90° C. to 180° C. and at a pressure of between 1 and 100 Kg/cm$^2$, in particular between 10 and 100 Kg/cm$^2$.

The feeding rate of the gaseous reagents, which can be expressed as an hourly space velocity of the gas (GHSV, h$^{-1}$), is between 100 and 10000 h$^{-1}$, in particular between 100 and 2500 h$^{-1}$.

In the preferred form of the procedure of the present invention, the alcohols having general formula (II) are selected from: methanol, ethanol, n-propanol, isopropanol, n-butanol, isobutanol; wherefor R or R', in general formula (II), represent methyl, ethyl, n-propyl, isopropyl, n-butyl, isobutyl respectively. The organic carbonates thus obtained are: dimethyl carbonate, diethyl carbonate, di-n-propyl carbonate, di-isopropyl carbonate, di-n-butyl carbonate, di-isobutyl carbonate.

The catalyst, as previously described, is composed of the oxides, salts, more preferably non-halogenated, or complexes of cobalt, used alone or combined with each other, both as single constituents of the catalysts, and supported on inert materials which are stable under the reaction conditions, such as, for example, MgO, SiO$_2$, Al₂O₃, TiO₂, ZnO, zeolites, or more preferably, active carbon.

The salts or complexes of cobalt used as catalysts in the carbonylation procedure can be supported on the inert material using any of the impregnation techniques known in the art, such as, for example, that described in: "Experimental Methods in Catalytic Research", vol. II, published by R.B. Anderson and P.T. Dawson, Academic Press, N.Y., 1978.

The quantity of catalyst used in the procedure of impregnation in the present invention, is not limitative and is, normally more than 0.1% calculated with respect to the metal as such, generally between 0.5% (w/w) and 50% (w/w).

Catalysts used as such or combined with each other, both alone and supported on inert material, in the procedure of the present invention are: oxides of cobalt such as: CoO and Co₂O₃; salts and complexes of cobalt, possibly in their hydrate form. In the salts and complexes of cobalt, the cobalt is preferably a bivalent or trivalent cobalt ion and the anion is preferably an organic carboxylate, beta-diketone or a Schiff base containing a functional group of oxygen as donor. Schiff base refers to the condensation product of a primary amine with a carbonylic compound, as illustrated for example by S. Dayagi and Y. Degani in "Methods of Formation of the Carbon-Nitrogen Double Bond", pages 61-130, in "The Chemistry of Functional Groups", Ed. S. Patai, Wiley-Interscience. This reaction is typically represented as follows:

$$R^1R^2CO + R^3NH_2 \rightarrow R^1R^2C=CNR^3 + H_2O$$

wherein $R^1$, $R^2$ and $R^3$ represent organic radicals.

Examples of carboxylate anions suitable for the purpose are represented by the following formulae:

$$R_1-COO^-; R_2-[COO^-]_2; R_3-[COO^-]_3; R_4-[COO^-]_4;$$

wherein $R_1$, $R_2$, $R_3$ and $R_4$ are monovalent, bivalent, trivalent and tetravalent organic radicals respectively, containing up to 20 carbon atoms and which may additionally contain one or more non-carboxylic oxygen atoms, nitrogen atoms, sulphur atoms and halogens. Non-limitative examples are:

$R_1 =$ H—, CH₃—, CH₃—CH₂—, CH₃(CH₂)₂—, CH₃(CH₂)₃—, CH₂=CH—, (CH₃)₂CH—, (CH₃)₂CH—CH₂—,

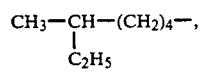

and the cyclohexyl radicals, phenyl radicals and phenyl radicals substituted with alkyl, aryl, halogen, alkoxy or nitro- or cyano-substituted;

$R_2 =$ —CH₂—, —CH₂—CH₂—, —CH=CH—, —CH₂—CH₂—CH₂—, —CH₂—NH—CH₂—CH₂—NH—CH₂—, —CH₂—(CH₂)₂—NH—(CH₂)₂—CH₂—, —CH₂—(CH₂)₂—CH₂—, and —CH(OH)—CH(OH)—, and the phenylene or phenylene substituted radicals, or $R_2$ is a direct bond;

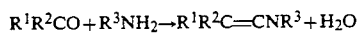

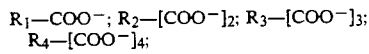

Examples of beta-diketonate anions suitable for the purpose are represented by the formula:

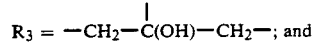

wherein $R_5$, $R_6$ and $R_7$, each independently, represent a hydrogen atom or an aliphatic, cycloaliphatic or aromatic radical containing up to 10 carbon atoms, and may additionally contain one or more non-carbonylic oxygen atoms, nitrogen atoms, sulphur atoms and halogens. Among the beta-diketonates acetylacetonate is particularly preferred:

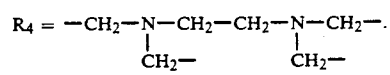

Examples of Schiff base anions suitable for the purpose are those represented by the following formulae:

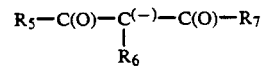

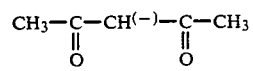

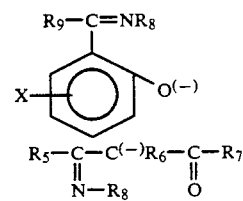

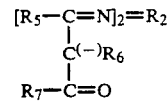

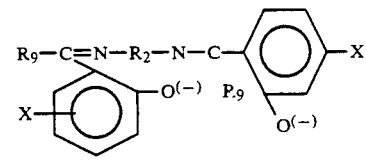

wherein $R_2$, $R_5$, $R_6$, $R_7$ are as defined above, $R_8$ represents an aliphatic, cycloaliphatic or aromatic radical containing up to 10 carbon atoms, $R_9$ represents the hydrogen atom or has the same meaning as $R_8$ and X represents an alkyl, aryl, alkoxy, nitro, cyano, amino radical or a halogen atom.

In addition to the carboxylate anion, beta-diketonate or Schiff base and cobalt, the catalyst of the present invention may additionally contain a nitrogenous ligand, either monofunctional or polyfunctional, such as pyridine, dipyridyl, phenanthroline, tetramethylethylendiamine and ethylendiamine, and/or an alkaline or earth alkaline metal cation, such as sodium and barium. Examples of another class of compounds suitable are chelate complexes of cobalt with ligands containing at least one pyridinic ring, which can be defined by the following formulae:

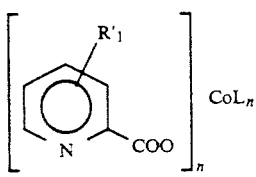

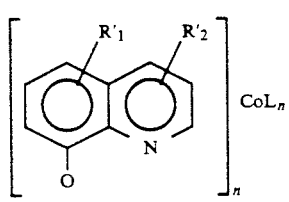

wherein:
n is an integer between 1 and 3;
m is an integer between 0 and 5;
R′₁ and R′₂ the same or different, represent a hydrogen atom or a halogen atom selected from chlorine, bromine or iodine, or a $C_1$-$C_{20}$ alkyl, alkoxyl, aryl or heteroalkyl radical;

L represents a secondary ligand which can be a nitrogenous ligand either mono or polyfunctional, neutral or anionic, such as for example pyridine, phenanthroline, piperydine, quinoline and isoquinoline, or an oxygenated ligand, either mono or polyfunctional, such as $H_2O$, —OH, —O—COO—R′₃ wherein R′₃ represents $C_1$-$C_5$ alkyl, —OCH₃ and CH₃—CO—CH$^{(-)}$—CO—CH₃. Specific examples of catalysts suitable for the purposes of the present invention are: cobalt(II) acetate, Co(CH₃COO)₂; cobalt(III) acetate, CO(CH₃COO)₃; cobalt(II) acetylacetonate; cobalt(III) acetylacetonate; sodium and cobalt(II) acetylacetonate; cobalt(II) acetylacetonate bipyridyl; cobalt(II) acetylacetonate phenanthroline; ethylendiamine sodium and cobalt(III) tetraacetate; ethylendiamine barium and cobalt(III) tetraacetate; cobalt(II) citrate; cobalt(II) oxalate; chelate complexes of cobalt with Schiff bases such as:

[Co(SALEN)]₂.H₂O;
wherein SALEN represents:

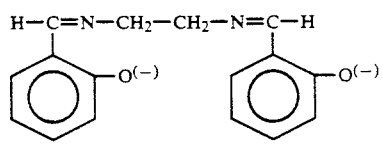

Co(SALPROPEN);
wherein SALPROPEN represents:

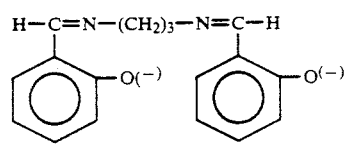

Co(ACACEN);
wherein ACACEN represents:

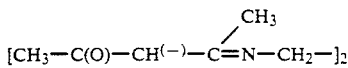

Co(SALOPH);
wherein SALOPH represents:

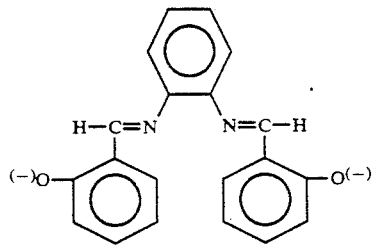

Specific examples of chelate complexes of cobalt with ligands containing at least one pyridinic ring as described above are:

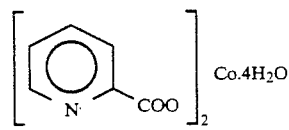

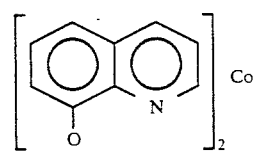

At the end of the procedure described above, the organic carbonate is recovered from the reaction mixture thus obtained using the known techniques, such as condensation operations also partial or fractionated, distillation, de-mixing, selective membrane permeation, etc. Any possible untransformed reagents are recycled in the reaction system.

The procedure of the present invention can be carried out either in a fluid or fixed bed and can be either continuous or batch. In particular a continuous process is carried out in a fixed bed reactor.

The following examples provide a better illustration of the present invention but do not limit it in any way.

EXAMPLE 1

1.9 g of Co(CH₃COO)₂.4H₂O dissolved in water, are supported on 15 g of SiO₂ (Type 432, produced and sold by GRACE) having a pore diameter of 0.6–1.4 nm; surface area: 320m²/g; specific pore volume: 1.2 ml/g; using standard impregnation techniques.

After drying at 90° C. for 24 hours under vacuum, the catalyst is analysed and the content by weight of cobalt is calculated and found to be 3%.

An inox steel reactor having a length of 33 cm and diameter of 1.12 cm is filled with carborundum up to 20 cm, 12 ml of the above catalyst are subsequently added.

The reactor is heated to 130° C. and pressurized at 15 Kg/cm² with carbon monoxide. 54 μl/min. of methanol which are added before entering the reactor, to 80 ml/min. of carbon monoxide and 13 ml/min. of oxygen (GHSV of 465 h⁻¹), are sent through a liquid chromatography (LC) pump, into a vaporizer kept at a temperature of 130° C.

The reaction products thus obtained, are condensed and collected in a cold trap at −78° C. and subsequently analysed by gas-chromatography.

The productivity of dimethylcarbonate is equal to 0.6 mmoles/h.

EXAMPLE 2

17.1 g of Co(pic)$_2$.4H$_2$O (pic=anion of picolinic acid) dissolved in 200 ml of hot water are put in contact with 15 g of zinc oxide. When the water has been evaporated and after drying at 100° C. for 24 hours under vacuum, the catalyst is obtained. The content of cobalt equal to 8.2% is determined by analysis.

A stainless steel reactor having a length of 17 cm and diameter of 1.12 cm is filled with 16 ml of the catalyst described above. It is heated to 135° C. and pressurized at 30 Kg/cm$^2$ with carbon monoxide. 20 μl/min of methanol added to 50 ml/min of carbon monoxide and 7 ml/min of oxygen before entering the reactor (GHSV=255h$^{-1}$) are sent into a vaporizer kept at 150° C. by means of a liquid chromatography (LC) pump. The reaction products thus obtained are condensed and collected in a cold trap at −78° C. and subsequently analysed by gas-chromatography. A productivity of 0.31 mmoles/h of dimethylcarbonate is determined.

EXAMPLE 3

17.1 g of Co(pic)$_2$.4H$_2$O (pic=anion of picolinic acid) dissolved in 200 ml of hot water are put in contact with 15 g of active carbon Chemviron 20-40 mesh. When the water has been evaporated and after drying at 100° C. for 24 hours under vacuum, the catalyst is obtained. The content of cobalt equal to 7.9% is determined by analysis.

A stainless steel reactor having a length of 17 cm and diameter of 1.12 cm is filled with 16 ml of the catalyst described above. It is heated to 135° C. and pressurized at 30 Kg/cm$^2$ with carbon monoxide. 20 μl/min of methanol added to 50 ml/min of carbon monoxide and 7 ml/min of oxygen before entering the reactor (GHSV=255h$^{-1}$) are sent into a vaporizer kept at 150° C. by means of a liquid chromatography (LC) pump. The reaction products thus obtained are condensed and collected in a cold trap at −78° C. and subsequently analysed by gas-chromatography. A productivity of 1.35 mmoles/h of dimethylcarbonate is determined.

EXAMPLE 4

11.4 g of Co(pic)$_2$.4H$_2$O (pic=anion of picolinic acid) dissolved in 150 ml of hot water are put in contact with 20 g of active carbon Chemviron 20-40 mesh. When the water has been evaporated and after drying at 100° C. for 24 hours under vacuum, the catalyst is obtained. The content of cobalt equal to 5.4% is determined by analysis.

A stainless steel reactor having a length of 17 cm and diameter of 1.12 cm is filled with 16 ml of the catalyst described above. It is heated to 135° C. and pressurized at 30 Kg/cm$^2$ with carbon monoxide. 20 μl/min of methanol added to 50 ml/min of carbon monoxide and 7 ml/min of oxygen before entering the reactor (GHSV=255h$^{-1}$) are sent into a vaporizer kept at 150° C. by means of a liquid chromatography (LC) pump. The reaction products thus obtained are condensed and collected in a cold trap at −78° C. and subsequently analysed by gas-chromatography. A productivity of 0.97 mmoles/h of dimethylcarbonate is determined.

EXAMPLE 5

6.7 g of Co(acac)$_3$(acac=acetylacetonate) dissolved in 50 ml of methanol are put in contact with 12.5 g of active carbon Chemviron 20-40 mesh. When the methanol has been evaporated and after drying at 100° C. for 24 hours under vacuum, the catalyst is obtained. The content of cobalt equal to 5.5% is determined by analysis.

A stainless steel reactor having a length of 17 cm and diameter of 1.12 cm is filled with 16.5 ml of the catalyst described above. It is heated to 135° C. and pressurized at 30 Kg/cm$^2$ with carbon monoxide. 20 μl/min of methanol added to 50 ml/min of carbon monoxide and 7 ml/min of oxygen before entering the reactor (GHSV=247h$^{-1}$) are sent into a vaporizer kept at 150° C. by means of a liquid chromatography (LC) pump. The reaction products thus obtained are condensed and collected in a cold trap at −78° C. and subsequently analysed by gas-chromatography. A productivity of 0.28 mmoles/h of dimethylcarbonate is determined.

EXAMPLE 6

8.6 g of Co(pic)$_2$.(bipyridyl) (pic=anion of picolinic acid) dissolved in 100 ml of hot water are put in contact with 12.5 g of active carbon Chemviron 20-40 mesh. When the methanol has been evaporated and after drying at 100° C. for 24 hours under vacuum, the catalyst is obtained. The content of cobalt equal to 4.9% is determined by analysis.

A stainless steel reactor having a length of 17 cm and diameter of 1.12 cm is filled with 16.5 ml of the catalyst described above. It is heated to 135° C. and pressurized at 30 Kg/cm$^2$ with carbon monoxide. 20 μl/min of methanol added to 50 ml/min of carbon monoxide and 7 ml/min of oxygen before entering the reactor (GHSV=247h$^{-1}$) are sent into a vaporizer kept at 150° C. by means of a liquid chromatography (LC) pump. The reaction products thus obtained are condensed and collected in a cold trap at −78° C. and subsequently analysed by gas-chromatography. A productivity of 1.32 mmoles/h of dimethylcarbonate is determined.

EXAMPLE 7

2.8 g of cobalt(II) oxalate dissolved in 500 ml of heated concentrated ammonia are put in contact with 12.5 g of active carbon Chemviron 20-40 mesh. When the ammonia has been evaporated and after drying at 100° C. for 12 hours under vacuum, the catalyst is obtained. The content of cobalt equal to 4.5% is determined by analysis.

A stainless steel reactor having a length of 17 cm and diameter of 1.12 cm is filled with 15 ml of the catalyst described above. It is heated to 135° C. and pressurized at 30 Kg/cm$^2$ with carbon monoxide.

2.4 ml/h of methanol added to 90 ml/min of carbon monoxide and 10 ml/min of oxygen before entering the reactor (GHSV=488h$^{-1}$) are sent into a vaporizer kept at 150° C. by means of a liquid chromatography (LC) pump.

The reaction products thus obtained are condensed and collected in a cold trap at −78° C. and subsequently analysed by gas-chromatography.

A productivity of 0.25 g/h (2.78 mmoles/h) of dimethylcarbonate is determined, with a conversion of the methanol equal to 9%.

We claim:

1. Catalytic procedure in gas phase for the preparation of a symmetrical or asymmetrical organic carbonate having the general formula (I):

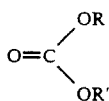

wherein R and R', the same or different, represent a $C_1$–$C_4$ alkyl radical, linear or branched, which includes reacting at least one alcohol having the general formula (II):

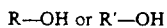

with carbon monoxide and oxygen in the presence of a catalyst comprised of one or more non-halogenated cobalt-containing compounds selected from cobalt oxides, cobalt salts, cobalt complexes, and mixtures of the foregoing.

2. Procedure according to claim 1, wherein the molar ratio between the carbon monoxide and alcohol is between 1:1 and 1000:1.

3. Procedure according to claim 1, wherein the molar ratio between the oxygen and the alcohol is between 2:1 and 1:100.

4. Procedure according to claim 1, wherein the ratio in volume between the oxygen and the carbon monoxide is between 1:1 and 1:100.

5. Procedure according to claim 1, wherein the reaction is carried out at a temperature ranging from 20° C. to 250° C..

6. Procedure according to claim 1, wherein the reaction is carried out at a pressure of between 1 and 100 $Kg/cm^2$.

7. Procedure according to claim 1, wherein the feeding rate of the gaseous reagents, expressed as an hourly space velocity of the gas (GHSV, $h^{-1}$), is between 100 and 10000 $h^{-1}$.

8. Procedure according to claim 1, wherein the alcohols having general formula (II) are selected from: methanol, ethanol, n-propanol, isopropanol, n-butanol, isobutanol.

9. Procedure according to claim 1, wherein the catalyst is supported on inert materials which are stable under the reaction conditions.

10. Procedure according to claim 9, wherein the catalysts are: cobalt oxides; salts and complexes of cobalt; chelate complexes of cobalt with organic carboxylates; chelate complexes of cobalt with beta-diketonates; chelate complexes of cobalt with Schiff bases; chelate complexes of cobalt with ligands containing at least one pyridinic ring.

11. Procedure according to claim 9, wherein the inert material is selected from the group consisting of MgO, $SiO_2$, $Al_2O_3$, $TiO_2$, ZnO, zeolites and active carbon.